United States Patent [19]

Aliev et al.

[11] 4,255,350

[45] Mar. 10, 1981

[54] PROCESS FOR PREPARING METHYL ISOCYANATE

[76] Inventors: Vagab S. Aliev, ulitsa Nizami, 66, kv. 10; Sakhib M. O. Aliev, ulitsa Barinova, 12, kv. 31; Farrukh R. O. Gadzhiev, ulitsa Druzhba-Molodezhi, 47, kv. 48; Novruz I. O. Guseinov, poselok novy Akhmedly, proezd 1730, 13V, kv. 96; Shamkhal A. M. O. Mamedov, ulitsa Malygina, 1, kv. 31; Medzhid A. Mardanov, ulitsa 28, Aprelya, 72, kv. 27; Rafail S. Sverdlov, Rabochy proezd, 5, kv. 39; Dzhavid N. O. Khydyrov, Leningradsky prospekt, 138, kv. 10, all of Baku, U.S.S.R.

[21] Appl. No.: 72,418

[22] Filed: Sep. 4, 1979

[51] Int. Cl.$^3$ ............................................. C07C 118/00
[52] U.S. Cl. ................................................. 260/453 P
[58] Field of Search ..................................... 260/453 P

[56] References Cited

U.S. PATENT DOCUMENTS

| 3,584,028 | 6/1971 | Argabright et al. | 260/453 P |
| 3,644,461 | 2/1972 | Rennells | 260/453 P |

FOREIGN PATENT DOCUMENTS

| 48-1652 | 1/1973 | Japan . |
| 48-20534 | 6/1973 | Japan . |

*Primary Examiner*—Dolph H. Torrence
*Attorney, Agent, or Firm*—Fleit & Jacobson

[57] ABSTRACT

The process for preparing methyl isocyanate includes feeding methyl halide through a reaction mixture at a rate of 0.5 to 3 moles of methyl halide per mole of cyanate per hour, the contact time being 1 to 4 min and a molar ratio of an organic solvent to methyl halide being (3 to 5):1 with subsequent withdrawal of the product out of the reaction zone.

6 Claims, No Drawings

PROCESS FOR PREPARING METHYL ISOCYANATE

BACKGROUND OF THE INVENTION

1. Field of the Invention

This invention relates to processes for preparing isocyanates and more particularly to the process of preparing methyl isocyanate which is useful as starting material in the manufacture of e.g. N-methylcarbamino acid esters possessing a wide range of the activity against insects.

2. Description of the Prior Art

Isocyanates currently find extensive application in chemical industry. Development of processes for preparing isocyanates is in progress now, and is aimed at providing compositions and reaction conditions which offer higher yields.

Known in the art is a process for preparing methyl isocyanates (U.S. Pat. No. 3,644,461) by reacting phosgene with methyl amine or with chlorine hydrate of the same at 250° C. giving rise to a formation of N-methyl carbamoyl chloride and decomposition thereof until methyl isocyanate is formed:

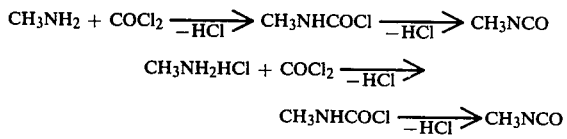

Gaseous methyl amine and phosgene are reacted at the first stage in a continuous fashion at a temperature range of 350° to 400° C. and atmospheric pressure. The reaction gases, which are represented by N-methyl carbamoyl chloride and HCl, are flown through a tower wherein carbon tetrachloride cooled to $-10°$ C. is sprayed to cool the reaction gases to 65°–70° C.

A solution of methyl carbamoyl chloride in carbon tetrachloride thus obtained is passed to a tower to strip unreacted phosgene. Next, hydrogen chloride is split off methyl carbamoyl chloride present in solution with carbon tetrachloride by methyl aniline at 45° to 50° C. to produce methyl isocyanate. Methyl isocyanate is prepared in two consecutive towers. The yield of methyl isocyanate is $\approx 90\%$ of the theoretical. The methyl isocyanate obtained contains 98% of the basic substance and 2% carbon tetrachloride.

Though a rather high yield of methyl isocyanate is provided by this process, it still follows a multi-stage procedure, may be carried out with a complicated equipment, is based on costly and what is extremely important on highly toxic starting materials. Also, the hydrochloric acid produced in the process causes the equipment to corrode. Difficulties are also met with in regeneration of auxiliary substances involved in the process.

Thus, waste materials from the regeneration of dimethyl aniline and carbon tetrachloride need to be subjected to thermal decomposition with resulting environmental pollution.

Other prior art processes for preparing methyl isocyanate include such as by thermally decomposing N,N-diphenyl-N'-methylurea at 240° to 249° C. (Siefken, Ann. (1949) 562, 75) or phenyl-N-methyl carbamate at 240° to 250° C. (Japanese Patent Publication No. 1652-73).

Methyl isocyanate may also be prepared by reacting methyl amine with diphenyl carbonate at a temperature of 200° C. but lower than the boiling point of diaryl carbonate (Japanese Patent Publication No. 20534-73) or by reacting N,N-dimethyl area with diaryl carbonate in a mole ratio of 1:1.5 to 1.4 and temperature of 200°–300° C. (Japanese Patent Publication No. 1652-73).

To practice these processes, however, there is need for scarce materials, which are produced in the processes involving phosgene and scarce amines.

U.S. Pat. No. 3,584,028 discloses a process for the manufacture of organic isocyanates having from $C_1$ to $C_{20}$ in the carbon group comprising reacting an alkali metal cyanate and/or alkaline earth metal cyanate with organic chlorides in an organic solvent in the presence of a catalyst, namely an alkali metal bromide or alkaline earth metal bromide, or alkali metal iodide, or alkaline earth metal iodide at elevated temperature.

To practice the process a reaction mixture conjointly contains 0.5 to 5 moles, preferably 0.8 to 1 mole of the cyanates, 0.01 to 10 moles, preferably 0.5 to 0.25 mole of the catalyst, 10 to 100 moles, preferably 25 to 50 moles of the organic solvent, per 1 mole of the organic chloride. The reaction temperature is 25° to 300° C., preferably 50° to 150° C., pressure may be from below 1 to 703 kg/cm², and the time of contacting equals 50 min.

Examples show benzyl chloride, allyl chloride, N-octyl chloride as the organic chlorides.

The last specified process does not involve highly toxic substances. But the yield of isocyanates is from 6.8 to 55%, the remainder 45% or more being isocyanates. The time (50 min.) of contacting of the cyanates with halides, due to which isocyanate obtained is polymerized is a reason, among others equally important, for the formation of isocyanurates.

This process is also disclosed as suitable for preparing isocyanate having 1 carbon atom, i.e. methyl isocyanate.

In this instance methyl chloride is used as organic chloride.

Since methyl isocyanate among alkyl isocyanates is the most sensitive to heating and to the presence of salts the cations of which being the alkali metals and the alkaline earth metals, while anions being halogenides, OCN', CO''₃, etc., the yield of methyl isocyanate is expected to be still lower.

SUMMARY OF THE INVENTION

It is an object of the invention to provide for higher yields of methyl isocyanates.

It is still another object of the invention to increase the efficiency of the process for preparing isocyanate.

It is also an object of the invention to decrease the consumption of an organic solvent.

An object of the invention is to increase the yield of methyl isocyanate by changing the reaction conditions between the reaction medium and methyl halide.

These and other objects of the invention are attained in that the prior art process for preparing methyl isocyanate by reacting an alkali metal cyanate and/or alkaline earth metal cyanate with methyl halide in the presence of a catalyst, namely an alkali metal bromide, or alkali metal iodide, or alkaline earth metal iodide at elevated temperature, according to the invention, comprises contacting of a reaction mixture with methyl halides at 0.5 to 3 moles of the methyl halide per 1 mole of cyanate per hour for from 1 to 4 minutes and with a ratio of an organic solvent to the methyl halide of (3 to 5):1 followed by continuous withdrawal of the product being obtained from the reaction zone.

Methyl isocyanate is sensitive to heating and to the presence of salts the cations of which being the alkali metals and the alkaline-earth metals, while anions being halogenides, $OCN'$, $CO''_3$, etc.

Therefore, to obtain higher yields of methyl isocyanate, the time of contact of methyl halides with a reaction mixture is to be decreased.

The reaction mixture as herein understood contains an alkali metal cyanate and/or alkaline earth metal cyanate suspended in an organic solvent and a catalyst, namely an alkali metal bromide, or alkaline earth metal bromide, or alkali metal iodide, or alkaline earth metal iodide, dissolved in the organic solvent. Contact duration for 1 to 4 minutes provides for higher yields of isocyanate, while continuous withdrawal of the product from the reaction zone precludes polymerization thereof.

The contact time specified is ensured in that the halide methyl is fed at 0.5 to 3 moles of methyl halide per 1 mole of cyanate per hour. In doing this, the components are brought into contact more rapidly, and the area of contact gets increased, which also leads to a higher yield of methyl isocyanates.

The process permits the consumption of the organic solvent to get decreased and the process to be carried out at the ratio of the organic solvent to methyl halide as 3 to 5:1 in contrast to the prior art process showing from 10 to 100 moles of the organic solvent per mole of methyl halide.

As the ratio of the organic solvent to methyl halide gets increased so methyl isocyanate dissolves in the organic solvent and it is impossible to separate methyl isocyanate even at temperatures up to 150° C. and higher, and, alternatively, dissolved methyl isocyanate polymerizes into trimethylisocyanurate with a consequence that the yield of methyl isocyanate decreases to about 50%. A decrease in the yield of isocyanate occurs again when the ratio of the organic solvent to methyl halide is decreased.

Prior to feeding methyl halide, the reaction mixture, while being agitated, is preferably heated to a temperature range of 120° to 140° C. and then cooled to 60° to 70° C. and from 0.5 to 2 moles of methyl halide fed to the reaction mixture followed by heating up to between 110° and 120° C. and simultaneously feeding the remainder of methyl halide.

The process thus modified provides for higher yields of methyl isocyanate with a higher degree of purity, since prior to feeding methyl halide, the reaction mixture is made free from moisture and amines which cause cyanate hydrolysis and methyl isocyanate polymerization.

It is advisable that prior to feeding methyl halide, moisture and amine admixtures be removed from the reaction mixture by adding thereto a low-boiling solvent, namely petroleum ether, or benzene, or toluene, or a mixture of benzene and toluene, followed by heating the reaction mixture, while agitating the same, to a temperature of 120° to 140° C., cooling down to between 60° and 70° C., contacting with 0.5 to 2 moles of the methyl halide, and reheating to a temperature of 110° to 120° C. with simultaneously contacting the reaction mixture with the remainder of the methyl halide.

This modification of the process makes it possible to intensify preparation of methyl isocyanate as far as amine admixtures and moisture are removed from the reaction mixture more rapidly and together with a low-boiling solvent at elevated temperature.

For best results, the reaction mixture is agitated by way of feeding nitrogen gas which is inert to the reaction mixture.

While agitating the reaction mixture, inert gas assists in rapid removal of moisture and amines from the reaction zone.

DESCRIPTION OF THE PREFERRED EMBODIMENTS

Description of practices with the process of the invention follows.

To carry out the process, use is made of a tower-like reactor having a provision for electric heating and an arrangement for distributing a gaseous methyl halide housed within the reactor lower section.

The process is started by loading the reactor with an organic solvent composed of both polar and nonpolar solvents, a catalyst such as an alkali metal bromide, or alkaline earth metal bromide, or alkali metal iodide, or alkaline earth metal iodide, and alkali metal cyanate and/or alkaline metal cyanate.

The process of the invention utilizes hydrocarbons having a boiling point at least 100° C. as the nonpolar solvent. One of such powerful nonpolar solvents is meta-xylene, and N,N-dialkylsubstituted amides such as dimethylformamide are employed as the polar solvent.

The cyanate suitable for the process may contain up to 25% carbonate admixtures. KCl as a by-product of methyl isocyanate contains $K_2CO_3$. The latter may be transformed into KCl by an auxiliary treatment with HCl.

Having the reactor loaded, the electric heating is switched on and the reaction mixture is agitated. Agitation is effected by nitrogen gas inert to the reaction mixture and flown into the reactor by an impeller, while both can be simultaneously used as well.

Having the reaction mixture heated up to 120° to 140° C., methyl chloride, or methyl bromide, or methyl iodide begin to be fed at 1 to 3 moles (22.4 to 67.2 l) of the above compounds per 1 mole of cyanate per hour.

Methyl isocyanate preparation process may be practiced by heating the reaction mixture to a temperature of 120° to 140° C. with simultaneous agitation in order to remove amine admixtures and the moisture. Then the temperature gets lowered to 60° to 70° C., nitrogen gas feeding stops (if agitation is by nitrogen) and begins feeding 0.5 to 2 moles of methyl halide.

At the beginning of the process methyl halide dissolves in the reaction mixture, while no methyl isocyanate and other product are separated from the reaction zone. Now the temperature in the reactor spontaneously raises up to 90° to 100° C. and methyl isocyanate is separated to be withdrawn through a condenser and into a receiver.

Next the reactor temperature is raised in the range of 110° to 120° C. and the remainder of methyl halide is fed into the reactor.

Amine admixtures and moisture can be removed by introducing a low-boiling organic solvent such as petroleum ether, or benzene, or toluene, or a mixture of benzene and toluene into the reaction mixture prior to feeding methyl halide.

Then follows the heating-up of the reaction mixture to a temperature in the range of 120° to 10° C. with simultaneous agitation. Now the admixtures are removed from the reaction mixture together with a low-boiling-point solvent. The process is further run as hereinabove described.

The process is controlled by gas-liquid chromatography. Following the process termination, the reaction mixture is cooled down to 20° to 25° C. Alkali metal chloride formed in the reaction is separated from the solvents and from the catalyst dissolved in the solvents, by a centrifugal separator. A mixture of solvents and catalysts separated from the chloride may be recycled.

The yield of methyl isocyanate is 92 to 97% of the theoretical calculation based on cyanate used. Methyl isocyanate thus prepared may contain up to 2% of methyl chloride and methyl iodide. But the presence of these in methyl isocyanate does not interfere with the synthesis of a naphthyl ester of the N-methylcarbamide acid based on methyl isocyanate.

Now the invention is illustrated by the examples which follow.

EXAMPLE 1

To a reactor of 4 l capacity having 200 cm in height and 5 cm in diameter and electrically heated was added 530 g (5 mole) of meta-xylene. 730 g (10 mole) of dimethylformamide, 83 g (0.5 mole) of potassium iodide, 300 g of an industrial-grade potassium cyanate having particle size not more than 0.1 mm and containing 243 g (3 mole) of potassium cyanate and 57 g (0.41 mole) of potassium carbonate.

The mixture was agitated by feeding dry nitrogen into the reactor with simultaneous heating. The reactor temperature was elevated to 130° C. and 106 g (1 mole) of meta-xylene was isolated as an azeotrope of water and amines. The temperature in the reactor was then decreased to 60° C., the nitrogen feeding cut off and 151 g (3 mole) of methyl chloride was initiated to be fed at a rate of 22.4 l (1 mole) per mole of potassium cyanate per hour with a molar ratio of a solvent to methyl chloride being 5:1. The contact time was 2.5 min.

After 1.5 moles (75.75 g) of methyl chloride had been added the reactor temperature was being gradually increased up to 100° C. and there began to get isolated methyl isocyanate which was continuously being withdrawn through a condenser and out of the reactor. The temperature was then being gradually increased up to 120° C. and the remainder of methyl chloride was added. The yield of methyl isocyanate was 162.5 g or 95% of the theoretical. The purity of methyl isocyanate obtained was 98%.

The contents of the reactor was cooled down to 25° C. and a mixture of potassium chloride, potassium cyanate, and potassium carbonate was filtered out. The filtrate consisting of meta-xylene, dimethylformamide, and potassium iodide dissolved in the former two, was reused.

EXAMPLE 2

To the reactor specified in Example 1 was added 530 g (5 mole) of meta-xylene, 730 g (10 mole) of dimethylformamide, 75 g (0.5 mole) of sodium iodide, 238.5 g of an industrial-grade sodium cyanate having particle size 0.1 mm and containing 195 g (3 mole) of sodium cyanate and 43.5 g (0.40 mole) of sodium carbonate.

The mixture was agitated by feeding dry nitrogen into the reactor with simultaneous heating and increasing the reactor temperature up to 130° C.

Meta-xylene in an amount of about 106 g (1 mole) was isolated as an azeotrope of water and amines. The temperature in the reactor was then descreased to 60° C., the nitrogen feeding cut off and 151 g (3 mole) of methyl chloride was initiated to be fed at a rate of 22.4 l (1 mole) per mole of sodium cyanate per hour with a molal ratio of a solvent to methyl chloride being 5:1. The contact time was 2.5 min. After 1.5 moles (75.75 g) of methyl chloride had been added the reactor, temperature was being gradually increased up to 100° C. and there began to get isolated methyl isocyanate which was continuously being withdrawn through a condenser and to a receiver.

The reactor temperature was being gradually increased up to 120° C. and the remainder of methyl chloride was added.

The yield of methyl isocyanate was 157.3 g or 92% of the theoretical. The purity of methyl isocyanate obtained was 98%. The content of the reactor was cooled and was further processed according to Example 1.

EXAMPLE 3

To the reactor specified in Example 1 was added 730 g of dimethylformamide, 1060 g (10 mole) of ethylbenzene, 294 g (1 mole) of calcium iodide, 258 g of an industrial-grade calcium cyanate having particle size 0.1 mm and containing 248 g (2 mole) of calcium cyanate and 10 g (0.1 mole) of calcium carbonate. The mixture was agitated by feeding dry nitrogen into the reactor with simultaneously raising the temperature within the reactor up to 140° C.

Ethylbenzene in an amount of 212 g (2 mole) was isolated as an azeotrope of water and amines.

The mixture was further cooled down to 70° C., the nitrogen feeding cut off and 151 g (3 mole) of methyl chloride was initiated to be fed at a rate of 22.4 l (1 mole) per mole of calcium cyanate per hour with a molal ratio of a solvent to methyl chloride being 4:1. The contact time was 2.5 min. After 2.0 moles (101 g) of methyl chloride had been added the reactor temperature was being gradually increased up to 100° C. and there began to get isolated methyl isocyanate which was continuously being withdrawn through a condenser and to a receiver. The reactor temperature was then being gradually increased up to 120° C. and the remainder of methyl chloride was added.

The yield of methyl isocyanate was 211 g or 92.5% of the theoretical. The purity of methyl isocyanate obtained was 98.5%.

The content of the reactor was cooled down to 25° C. and was further processed according to Example 1.

EXAMPLE 4

To the reactor specified in Example 1 was added 300 g (2.5 mole) of mesitylene, 78 g (1 mole) of benzene, 365 g (5 mole) of dimethylformamide, 83 g (0.5 mole) of potassium iodide, 300 g of an industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating. The reactor temperature was elevated to 120° C. and 75 g ($\approx$1 mole) of benzene was isolated as an azeotrope of water and amines. The temperature in the reactor was then decreased to 70° C., the nitrogen feeding cut off and 151 g (3 mole) of methyl chloride was fed at a rate of 22.4 l (1 mole) per mole of potassium cyanate per hour with a molar ratio of a solvent to methyl chloride being 3:1. The contact time was 2.5 min. After 1.5 moles (75.75 g) of methyl chloride had been added the reactor temperature was being gradually increased up to 100° C. and there began to get isolated methyl isocyanate which was continuously being withdrawn through a condenser and to a receiver. The reactor temperature was then being gradually increased up to 120° C. and the remainder of CH₃Cl was added. The yield of methyl isocyanate was 165.9 g or 97% of the theoretical. The purity of methyl isocyanate obtained was 99.0%. The contents of the reactor was cooled down to 25° C. and was further processed according to Example 1.

EXAMPLE 5

To the reactor specified in Example 1 was added 335 g (2.5 mole) of diethylbenzene, 505 g (5 mole) of diethylformamide, 92 g (1 mole) of toluene, 83 g (0.5 mole) of potassium iodide, 300 g of an industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating. The reactor temperature was elevated to 130° C. and 92 g (1 mole) of toluene was isolated as an azeotrope of water and amines.

The temperature in the reactor was then decreased to 70° C., the nitrogen feeding cut off, and 151 g (3 mole) of methyl chloride was fed at a rate of 67.2 l (3 mole) per mole of potassium cyanate per hour with a molar ratio of a solvent to methyl chloride being 3:1. The contact time was 1.0 min. After 1.5 moles (75.75 g) of methyl chloride had been added the reactor temperature was being gradually increased up to 100° C., and there began to get isolated methyl isocyanate which was continuously being withdrawn through a condenser and to a receiver. The reactor temperature was then being gradually increased up to 120° C. and the remainder of methyl chloride was added.

The yield of methyl isocyanate was 164.2 g or 96% of the theoretical. The purity of methyl isocyanate obtained was 98.3%.

The contents of the reactor was cooled down to 25° C. and was further processed according to Example 1.

EXAMPLE 6

To the reactor specified in Example 1 was added 530 g (5 mole) of ethylbenzene, 72 g of petroleum ether, 730 g (10 mole) of dimethylformamide, 83 g (0.5 mole) of potassium iodide, 300 g of an industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating. The reactor temperature was elevated to 120° C., and 72 g of petroleum ether was isolated as an azeotrope of water and amines. The temperature in the reactor was then decreased to 65° C., the nitrogen feeding cut off, and 151 g (3 mole) of methyl chloride was fed at a rate of 22.3 l (1 mole) per mole of potassium cyanate per hour with a molar ratio of a solvent to methyl chloride being 5:1. The contact time was 2.5 min.

After 1.5 moles (75.75 g) of methyl chloride had been added, the reactor temperature was being gradually increased up to 90° C., and there began to get isolated methyl isocyanate which was continuously being withdrawn through a condenser and to a receiver. The reactor temperature was then being gradually increased up to 120° C. and the remainder of methyl chloride was added. The yield of methyl isocyanate was 160.7 g or 94% of the theoretical. The purity of methyl isocyanate obtained was 98%. The contents of the reactor was cooled down to 25° C. and was further processed according to Example 1.

EXAMPLE 7

To the reactor specified in Example 1 was added 985 g (5 mole) of diphenylformamide, 265 g (2.5 mole) of meta-xylene, 39 g (0.5 mole) of benzene, 46 g (0.5 mole) of toluene, 83 g (0.5 mole) of potassium iodide, 300 g of industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating. The reactor temperature was elevated to 130° C. and 86 g of mixture consisting of benzene and toluene (0.5 mole each) was isolated as an azeotrope of water and amines.

The temperature in the reactor was then decreased to 70° C., the nitrogen feeding cut off, and 151 g (3 mole) of methyl chloride was fed at a rate of 22.4 l (1 mole) per mole of potassium cyanate per hour with a molar ratio of a solvent to methyl chloride being 3:1. The contact time was 2.5 min. After 1 mole (50.5 g) of methyl chloride had been added, the reactor temperature was being gradually increased up to 90° C., and there began to get isolated methyl isocyanate which was continuously being withdrawn through a condenser and to a receiver. The reactor temperature was then being gradually increased up to 120° C., and the remainder of methyl chloride was added. The yield of methyl isocyanate was 160.3 g or 92% of the theoretical. The purity of methyl isocyanate obtained was 98%. The contents of the reactor was cooled down to 25° C. and was further processed according to Example 1.

EXAMPLE 8

To the reactor specified in Example 1 was added 600 g (5 mole) of ethyltoluene, 92 g (1 mole) of toluene, 870 g (10 mole) of dimethylacetamide, 83 g (0.5 mole) of potassium iodide, 300 g of industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating. The reactor temperature was elevated to 120° C., and 92 g (1 mole) of toluene was isolated as an azeotrope of water and amines. The temperature within the reactor was then decreased to 70° C., the nitrogen feeding cut off, and 151 g (3 mole) of methyl chloride was fed at a rate of 22.4 l (1 mole) per mole of potassium cyanate per hour with a molar ratio of a solvent to methyl chloride being 5:1.

The contact time was 2.5 min.

After 1.5 moles (75.75 g) of methyl chloride had been added, the temperature within the reactor was being gradually increased up to 100° C., and there began to get isolated methyl isocyanate which was continuously being withdrawn from the reactor through a condenser and to a receiver. The reactor temperature was then being gradually increased up to 120° C. and the remainder of methyl chloride was added. The yield of methyl isocyanate was 159 g or 93% of the theoretical. The purity of methyl isocyanate was 98%.

The contents of the reactor was cooled down to 25° C. and was further processed according to Example 1.

EXAMPLE 9

To the reactor specified in Example 1 was added 530 g (5 mole) of meta-xylene, 730 g (10 mole) of dimethylformamide, 60 g (0.5 mole) of potassium bromide, 300 g of industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating. The reactor temperature was elevated to 130° C., and 106 g (1 mole) of meta-xylene was isolated as an azeotrope of water and amines. The nitrogen feeding was then cut off, and 151 g (3 mole) of methyl chloride was fed at a rate of 22.4 l (1 mole) per mole of potassium cyanate per hour with a molar ratio of a solvent to methyl chloride being 5:1. The contact time was 2.5 min.

Methyl isocyanate being isolated was continuously withdrawn from the reactor through a condenser and to a receiver.

After feeding of 3 moles of methyl chloride had been finished, the content of the reactor was cooled down to 25° C. and was further processed according to Example 1.

The yield of methyl isocyanate was 137 g or 80% of the theoretical.

The purity of methyl isocyanate was 98%.

EXAMPLE 10

To the reactor specified in Example 1 was added 530 g (5 mole) of meta-xylene, 730 g (10 mole) of dimethylformamide, 51.5 g (0.5 mole) of sodium bromide, 238.5 g of industrial-grade sodium cyanate having particle size not more than 0.1 mm and containing 195 g (3 mole) of sodium cyanate and 43.5 g (0.40 mole) of sodium carbonate. The mixture was agitated by feeding dry nitrogen with simultaneous heating. The reactor temperature was elevated to 130° C., and 106 g (1 mole) was isolated as an azeotrope of water and amines. The nitrogen feeding was then cut off, and 151 g (3 mole) of methyl chloride was fed at a rate of 15 l (0.7 mole) per mole of sodium cyanate per hour with a molar ratio of a solvent to methyl chloride being 5:1.

The contact time was 4 min.

Methyl isocyanate being isolated was continuously withdrawn from the reactor through a condenser and to a receiver. After feeding of 3 moles of methyl chloride had been finished, the content of the reactor was cooled down to 25° C. and was further processed according to Example 1. The yield of methyl isocyanate was 128.3 g or 75% of the theoretical.

The purity of methyl isocyanate obtained was 98%.

EXAMPLE 11

To the reactor specified in Example 1 was added 530 g (5 mole) of ethylbenzene, 730 (10 mole) of dimethylformamide, 199.8 g (1 mole) of calcium bromide, 258 g of industrial-grade calcium cyanate having particle size not more than 0.1 mm and containing 248 g (2 mole) of calcium cyanate and 10 g (0.1 mole) of calcium carbonate. The mixture was agitated by feeding dry nitrogen into the reactor with simultaneous heating. The reactor temperature was elevated to 130° C., and 106 g (1 mole) of ethylbenzene was isolated as an azeotrope of water and amines. The nitrogen feeding was then cut off, and 151 g (3 mole) of methyl chloride was fed at a rate of 15 l (0.7 mole) per mole of calcium cyanate per hour with a molar ratio of a solvent to methyl chloride being 3:1.

The contact time was 4 min.

Methyl isocyanate being isolated was continuously withdrawn from the reactor through a condenser and to a receiver. After feeding of 5 moles of methyl chloride had been finished, the content of the reactor was cooled down to 25° C. and was further processed according to Example 1.

The yield of methyl isocyanate eas 178 g or 78% of the theoretical.

The purity of methyl isocyanate obtained was 98%.

EXAMPLE 12

To the reactor specified in Example 1 was added 530 g (5 mole) of ethylbenzene, 730 g (10 mole) of dimethylformamide, 166 g (1 mole) of potassium iodide, 150 g of industrial-grade potassium cyanate having particle size not more than 0.1 mm and containing 121.5 g (1.5 mole) of potassium cyanate and 28.5 g (0.20 mole) of potassium carbonate, and 129 g of industrial-grade calcium cyanate having particle size not more than 0.1 mm and containing 124 g (1 mole) of calcium cyanate and 5 g (0.05 mole) of calcium carbonate. The mixture was agitated by feeding dry nitrogen into the reactor with simultaneous heating. The reactor temperature was elevated to 130° C., and 106 g (1 mole) of ethylbenzene was isolated as an azeotrope of water and amines.

The temperature was then decreased to 60° C., the nitrogen feeding cut off, and 151 g (3 mole) of methyl chloride was initiated to be fed at a rate of 22.4 l (1 mole) per mole of mixture of cyanate of alkaline (K) and alkali-earth (Ca) metal per hour. Molar ratio of a solvent to methyl chloride was 5:1. The contact time was 2.5 min. After 1.5 moles (75.75 g) of methyl chloride had been added the reactor, the temperature was being gradually increased up to 100° C., and methyl isocyanate being formed was continuously isolated from the reactor through a condenser and to a receiver. The reactor temperature was being gradually increased up to 120° C. and the remainder of methyl chloride was added.

The yield of methyl isocyanate was 183 g or 92.8% of the theoretical (the calculation was carried out for the mixture of potassium and calcium cyanates). The purity of methyl isocyanate obtained was 98.2%.

The content of the reactor was cooled down to 25° C. and was further processed according to Example 1.

EXAMPLE 13

To the reactor specified in Example 1 was added 530 g (5 mole) of meta-xylene, 730 g (10 mole) of dimethylformamide, 300 g of industrial-grade potassium cyanate containing 243 g (3 mole) of potassium cyanate and 57 g (0.41 mole) of potassium carbonate having particle size not more than 0.1 mm.

Following the conditions specified in Example 1, 285 g (3 mole) of methyl bromide were being passed through the suspension (react on mixture). Methyl isocyanate in an amount of 150.4 g or 89% of the theoretical yield thereof was obtained as a result. The purity of methyl isocyanate obtained was 98.1%.

EXAMPLE 14

To the reactor specified in Example 1 was added 530 g (5 mole) of meta-xylene, 730 g (10 mole) of dimethylformamide, 300 g of industrial-grade potassium cyanate containing 243 g (3 mole) of potassium cyanate and 57 g (0.41 mole) potassium carbonate having particle size not more than 0.1 mm. Following the conditions specified in Example 1, 426 g (3 mole) of methyl iodide were being passed through the suspension. Methyl isocyanate in an amount of 163 g or 95.2% of the theoretical yield thereof was obtained as a result. The purity of methyl isocyanate obtained was 98%.

EXAMPLE 15 (COMPARATIVE)

To the reactor specified in Example 1 was added 530 g (5 mole) of meta-xylene, 730 g (10 mole) of dimethylformamide, 83 g (0.5 mole) of potassium iodide, 300 g of industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating.

The reactor temperature was elevated to 130° C., and 106 g (1 mole) of meta-xylene was isolated as an azeotrope of water and amines. The temperature in the reactor was then decreased to 60° C., the nitrogen feeding cut off, and 151 g (3 mole) of methyl chloride was fed at a rate of 7.6 l (0.35 mole) per mole of potassium cyanate per hour.

A molar ratio of a solvent to methyl chloride was 5:1.

The contact time was 8 min.

After 1.5 moles (75.75 g) of methyl chloride had been added, the reactor temperature was being gradually increased up to 100° C., and methyl isocyanate being formed was continuously withdrawn from the reactor through a condenser and to a receiver. The reactor temperature was then being gradually increased up to 120° C. The yield of methyl isocyanate was 96 g or 56% of the theoretical. The purity of methyl isocyanate obtained was 98%.

Thus, the increase in the contact time above the specified limit results in decrease in the yield of methyl isocyanate.

EXAMPLE 16 (COMPARATIVE)

To the reactor specified in Example 1 was added 530 g (5 mole) of meta-xylene, 730 g (10 mole) of dimethylformamide, 83 g (0.5 mole) of potassium iodide, 300 g of industrial-grade potassium cyanate having particle size not more than 0.1 mm and containing 243 g (3 mole) of potassium cyanate and 57 g (0.41 mole) of potassium carbonate. The mixture was agitated by feeding dry nitrogen into the reactor with simultaneous heating. The reactor temperature was elevated to 130° C., and 106 g (1 mole) of meta-xylene was isolated as an azeotrope of water and amines. The temperature in the reactor was then being gradually decreased to 70° C., the nitrogen feeding cut off, and 50.5 g (1 mole) of methyl chloride was fed at a rate of 22.4 l (1 mole) per mole of potassium cyanate per hour with a molar ratio of a solvent to methyl chloride being 15:1. The contact time was 2.5 min. After 0.5 mole (25.25 g) of methyl chloride had been added, the reactor temperature was being gradually increased up to 90° C. and methyl isocyanate being formed was continously withdrawn from the reactor through a condenser and to a receiver. The reactor temperature was then being gradually increased up to 120° C.

The yield of methyl isocyanate was 90 g or 52.5% of the theoretical. The purity of methyl isocyanate obtained was 98%.

Thus, the increase in solvent amount above the specified limit results in decrease in the yield of methyl isocyanate.

The invention has been described herein in terms of specific examples illustrating the process of obtaining methyl isocyanate at the lowest cost combined with the high yield. Also, numerous modifications known to those skilled in the art may be made in the invention. Thus, the invention is not limited by the specified examples and numerous variations and modifications may be made therein without departing from the spirit and scope thereof as set forth in the appended claims.

What is claimed is:

1. A process for preparing methyl isocyanate comprising the steps of providing in a reaction zone a reaction mixture consisting essentially of an organic solvent, an alkali metal cyanate or an alkaline earth metal cyanate and a catalyst selected from the group consisting of alkali metal bromides, alkaline earth metal bromides, alkali metal iodides and alkaline earth metal iodides; contacting the reaction mixture with a methyl halide selected from the group consisting of methyl chloride, methyl bromide and methyl iodide at a rate of from about 0.5 to 3 moles of methyl halide per mole of cyanate per hour for from about 1 to 4 minutes, the ratio of organic solvent to methyl halide being from about 3:1 to 5:1; and simultaneously withdrawing the methyl isocyanate from the reaction zone.

2. The process of claim 1, comprising the further steps of agitating the reaction mixture, heating the reaction mixture to a temperature of from about 120° to 140° C. and cooling the reaction mixture to a temperature between about 60° and 70° C. prior to the contacting step and wherein the contacting step comprises the steps of contacting the reaction mixture with from about 0.5 to 2 moles of methyl halide and heating the mixture to a temperature of from about 110° to 120° C., while simultaneously contacting the mixture with the remaining methyl halide.

3. The process of claim 2 wherein the agitating step is carried out by feeding nitrogen gas into the reaction mixture.

4. The process of claim 2, comprising the further step of adding a low-boiling solvent selected from the group consisting of petroleum ether, benzene, toluene and a mixture of benzene and toluene prior to initiation of the contacting step to remove moisture and amine admixtures from the reaction mixture.

5. The process of claim 4, wherein the agitating step is carried out by feeding nitrogen gas into the reaction mixture.

6. The process of any one of claims 1 to 5, wherein the organic solvent is a mixture of from 1 to 2 moles of an aprotic amide of an acid per mole of a nonpolar aromatic hydrocarbon.

* * * * *